United States Patent [19]

Kline

[11] Patent Number: 5,127,833
[45] Date of Patent: Jul. 7, 1992

[54] DENTAL SCALERS AND CURETTES HAVING IMPROVED CUTTING BLADE AND SHANK CONFIGURATIONS

[76] Inventor: Joseph M. Kline, 3501 N. Valley St., Arlington, Va. 22207

[21] Appl. No.: 470,784

[22] Filed: Jan. 26, 1990

[51] Int. Cl.$^5$ .................. A61C 17/00; A61C 3/00
[52] U.S. Cl. .................................. 433/143; 433/141
[58] Field of Search ........................ 433/143, 144, 119

[56] References Cited

U.S. PATENT DOCUMENTS

| D. 261,932 | 11/1981 | Bussiere | 433/143 X |
|---|---|---|---|
| 1,220,933 | 3/1917 | Bates . | |
| 1,402,525 | 1/1922 | Moseler | 433/143 |
| 1,497,749 | 6/1924 | Diack . | |
| 1,586,302 | 5/1926 | Funk | 433/141 X |
| 1,605,320 | 11/1926 | Bates . | |
| 1,605,321 | 11/1926 | Bates . | |
| 1,605,322 | 11/1926 | Bates . | |
| 2,002,245 | 5/1935 | McDaniel | 32/46 |
| 2,366,671 | 1/1945 | Montelius | 32/46 |
| 2,552,134 | 5/1951 | Berliner | 433/143 |
| 2,674,799 | 4/1954 | Fraser | 433/141 |
| 3,060,582 | 10/1962 | Kopp | 433/141 |
| 3,645,255 | 2/1972 | Robinson | 433/119 X |
| 3,930,173 | 12/1975 | Banko | 433/119 X |
| 4,365,957 | 12/1982 | Das | 433/144 |

OTHER PUBLICATIONS

Suter Dental Catalog, Jan. 1981 p. 5.
Thompson Dental Catalog, May 1984 p. 5).

*Primary Examiner*—Robert P. Swiatek
*Assistant Examiner*—Nicholas D. Lucchesi
*Attorney, Agent, or Firm*—Dowell & Dowell

[57] ABSTRACT

An improved dental scaler or curette wherein the cutting blade is spaced from the handle of the instrument by an arcuately formed shank portion which extends outwardly from the lower portion of the handle in a generally continuous arc to a relatively straight portion that extends transversely at an obtuse angel with respect to the plane of the arcuate shank and from which the cutting blade of the instrument extends at an acute angle with respect to the plane of the arcuate shank. In a further embodiment, the cutting blade includes a concave or generally V-shaped portion extending inwardly of the cutting edge thereof so as to form an elongated trough or trap in which material may be retained for removal during scaling or scraping of a tooth surface.

7 Claims, 2 Drawing Sheets

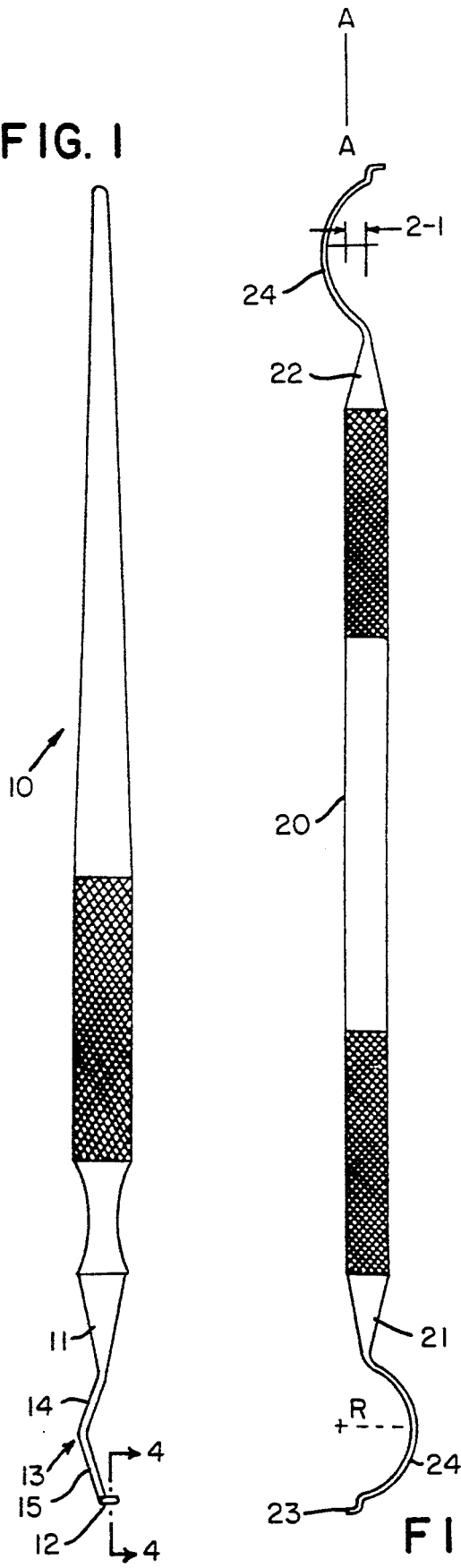
FIG. 1
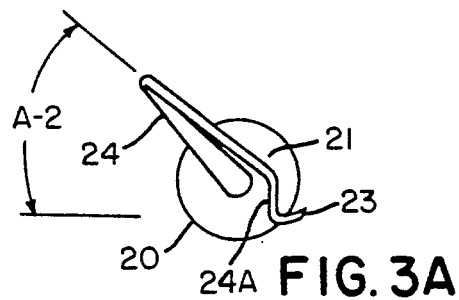
FIG. 3A
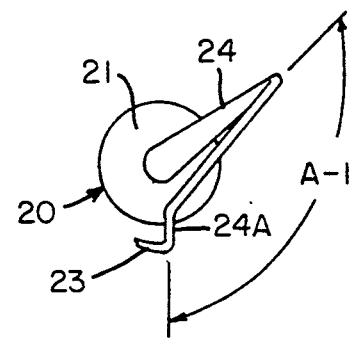
FIG. 3B
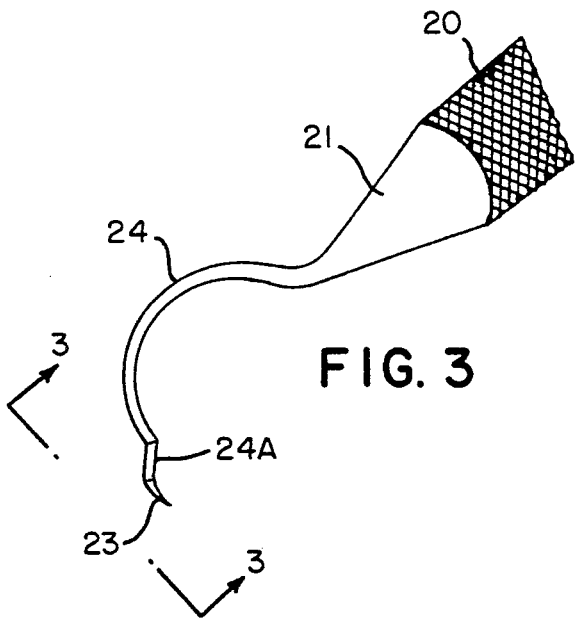
FIG. 2
FIG. 3

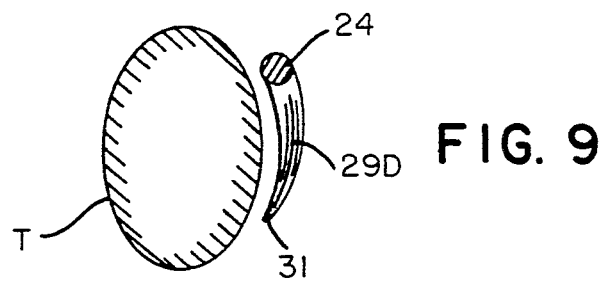
FIG. 9
FIG. 4
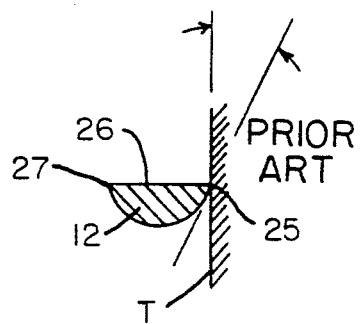
FIG. 4A
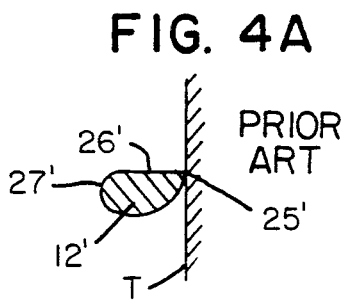
FIG. 5
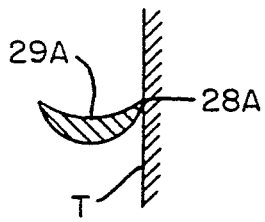
FIG. 6
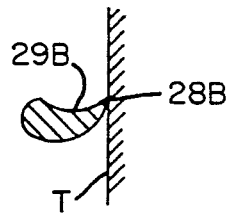
FIG. 10
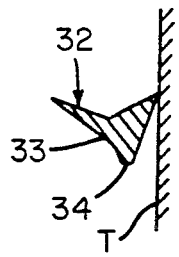
FIG. 7
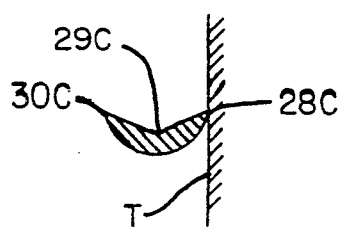
FIG. 8
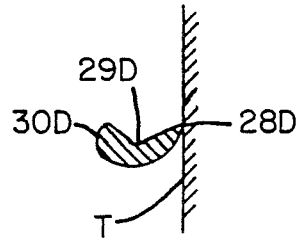

DENTAL SCALERS AND CURETTES HAVING IMPROVED CUTTING BLADE AND SHANK CONFIGURATIONS

BACKGROUND OF THE INVENTION

1. Field of the Invention

This invention is generally directed to dental instruments and more particularly to dental scalers and curettes wherein the cutting blade portion of the instruments are mounted to the handle of the instruments through an intermediate shank which is primarily of an elongated arcuate configuration which extends from the lower end of the instrument handle to a relatively short and transversely oriented straight segment from which the cutting blade extends. The shank segment is generally oriented at an obtuse angle with respect to the arcuate shank with the cutting blade being oriented at an acute angle with respect to the arcuate shank.

With this type of configuration, the arcuate shank acts as a barrier or spacing element to retain the cheek or tongue in space relationship to the tooth being scaled or curettaged. In another embodiment of the present invention, the upper surface of the cutting blades of the instrument are formed having concave, V-shaped or dished grooves therein which are spaced inwardly from the cutting edges of the blades for purposes of creating troughs or traps in which material scraped from a tooth or a root may be retained as the instrument is raised relative to the tooth. With this type of configuration, the accidental deposit of scraped tartar, debris or other material below the gum line during patient treatment is prevented.

In a further embodiment, the lower surface of the cutting blades of scalers or curettes are tapered downwardly to form a round wedge which will allow the blade to be gently urged between a tooth and the patient's gum.

2. History of the Related Art

Heretofore there have been many developments with regard to improving dental scalers and curettes. In applicant's co-pending patent application entitled Scalers for Periodontal Use, filed concurrently herewith, several types of prior art scaler configurations are discussed in greater detail. In addition, in the co-pending application, there is disclosed a unique configuration for dental instruments of the scaler and curette type which allows for a more efficient scaling of a patient's teeth by orientation of the cutting edges of the blades of such instruments to be compatible with the natural curvature of the tooth along a plane generally normal to the central or elongated axis of the tooth and wherein the curvature is such that an extended line of contact of the cutting edge and the tooth surface will be maintained when the instrument handle is oriented between angles of approximately 45 degrees and 90 degrees with respect to the axis of a tooth. Also, in the co-pending application, several types of cutting edge configurations are disclosed which enable the removal of excessive tartar or other debris or which are useful in treating irregular surface configurations.

Although conventional scalers and curettes provide for various forms of scaling action relative to the surface of a tooth, such structures have generally not adequately provided for the removal of scraped material during scaling and curettaging. Again, in applicant's co-pending application, a modified instrument blade is disclosed wherein the outer tip portion of the blade is vertically curved so as to assist in raising material that is scraped by acting as a spoon-like structure. Unfortunately, although this structure provides for some removal of scraped debris, it is not always efficient in providing maximum entrapment and removal of scraped tartar and other debris.

In addition to the foregoing, in most conventional scalers and curettes, the cutting blade is connected to the handle by an angular or offset shank portion which normally includes first and second diagonally oriented portions. Although such offset orientations of the blade with respect to the instrument handle allows the practitioner to observe the cutting blade more carefully during patient treatment, such structures have not been completely effective in retaining portions of the cheek or tongue from the area being treated thereby resulting in a partial obstruction of the area being treated as well as the possibility of such areas being accidentally injured during treatment.

Some examples of prior art dental scalers and curettes are disclosed in U.S. Pat. Nos. 1,220,933 to Bates, 1,605,320 to Bates, 1,605,321 to Bates, 1,605,322 to Bates, 1,497,749 to Djack, 2,002,245 to McDaniel and 2,366,671 to Montelius.

SUMMARY OF THE INVENTION

This invention is directed to dental instruments including scalers and curettes wherein the handle of the instrument is connected to the cutting blade by a continuous arcuate shank which extends from the lower portion of the handles to a relatively short straight segment from which the cutting blade extends. The shank segment is oriented at an obtuse angle with respect to the plane of the arcuate shank and depends approximately 3 to 6 mm therefrom. The cutting blade will extend generally normal to the shank segment. It is preferred that the radius of curvature of the shank be such that the shank extends outwardly with respect to the outer periphery of the handle of the instrument and further that the cutting blade extends generally transversely, and preferably at an acute angle with respect to the plane of the arcuate shank. With the elongated arcuate shank, it is possible to maintain a patient's cheek, tongue and other mouth tissue in spaced relationship from a tooth during treatment. The straight segment that goes to the blade is short on anterior instruments and longer as you proceed on posteriorly. In accordance with another embodiment of the present invention, the upper surface of the cutting blade of the implement is formed with an elongated trough, groove, or dished out area spaced inwardly from the cutting edge of the blade which recessed area may be utilized to receive and retain scraped tartar material after it has been dislodged by the cutting edge of the implement. Such recess will generally extend from adjacent the outermost tip of the cutting blade to a point which is spaced from the shank and which may be two or more millimeters in length.

In a further embodiment, the lower surface of a scaler or curette cutting blade is tapered to form a somewhat rounded wedge which may be used to gently separate the gum from a tooth during penetration of the cutting blade into a periodontal pocket.

It is a primary object of the present invention to provide dental instruments including scalers and curettes which provide for enhanced safety and comfort during scaling of a patient's teeth by enabling portions of the patient's cheek and tongue to be effectively spaced from the treatment area and to also allow the practitioner a better view of the surface area being scaled or curettaged.

It is a further object of the present invention to provide a dental instrument such as a scaler or curette wherein the handle and cutting blade are connected by an outwardly sweeping arcuate shank which is oriented with respect to the cutting blade and of a size to ensure that portions of the patient's cheek and tongue are retained spaced from the teeth during patient treatment to prevent accidental trauma to such areas.

It is another object of the present invention to provide a dental instrument such as a scaler or curette which provides for enhanced patient treatment and which further reduces the possibility of localized infection of treated areas including areas below a patient's gum line wherein the cutting blade includes a trough or trap for capturing or retaining material which is severed by the cutting edge of the instrument during patient treatment.

It is also an object of the present invention to provide dental scalers or curettes wherein the lower surface of the blades are downwardly tapered to provide a wedging action to permit a gentle penetration into periodontal pockets.

BRIEF DESCRIPTION OF THE DRAWINGS

FIG. 1 is a side elevational view of a conventional scaler including a generally V-shaped shank which connects the lower portion of the instrument handle to the instrument cutting blade.

FIG. 2 is a side elevational view of a dental instrument such as a scaler or curette incorporating the improved shank which connects the instrument handle to the cutting blade of the present invention.

FIG. 3 is an enlarged perspective view of one end of the instrument shown in FIG. 2 showing the arcuate configuration of the shank connecting the handle and the cutting blade.

FIG. 3A is an end view of the shank taken along lines 3—3 of FIG. 3.

FIG. 3B is an end view similar to FIG. 3A except showing the blade curvature for the tooth surface beginning with the upper left lingual.

FIG. 4 and FIG. 4a are cross-sectional views taken generally along lines 4—4 of FIG. 1 showing the cross-sectional configuration of a conventional curette and dental scaler with the cutting edges of such instruments engaging the surface of a tooth.

FIGS. 5-8 are four variations of cross-sectional configurations of the cutting blades of the present invention showing a trough, groove or dished area being provided adjacent the cutting edge of the blades which blades are shown as being in engagement with the surface of a tooth or root of a tooth.

FIG. 9 is a top plan view illustrating the length of the recessed portions of the cutting blades shown in FIGS. 5-8.

FIG. 10 is a cross-sectional view of a cutting blade having a downwardly tapered blunt lower surface for permitting a wedging action during dental pocket penetration.

DESCRIPTION OF THE PREFERRED EMBODIMENT

With continued reference to the drawings, a conventional dental scaler as shown in FIG. 1 includes a handle 10 having a lower tapered end portion 11 which is connected to the cutting blade 12 by way of a segmented shank 13 having upper and lower portions 14 and 15. It should be noted that the upper and lower portions 14 and 15 of the shank 13 are oriented at an angular relationship with respect to one another. With this type of structure, the practitioner is able to view the cutting edge associated with the cutting blade 12 during scaling or curettaging. Unfortunately, this structure does not provide for spacing adjacent tissue areas of the patient's mouth or the patient's tongue from the cutting blade during treatment.

With respect to FIGS. 2, 3, 3A and 3B, an improved dental instrument such as a scaler or curette is disclosed which includes an elongated handle 20 having lower and upper tapering end portions 21 and 22, respectively. For purposes of further discussion, it is envisioned that the embodiment of the present invention may be incorporated with scalers or curettes having cutting blade portions mounted at one or both ends thereof. In the embodiment of prior art scaler shown in FIG. 1, only a single cutting blade was associated with the handle whereas in the embodiment shown in FIG. 2, each end of the instrument is provided with a cutting blade. In the present invention, the cutting blades 23 are each connected to the end portions 21 and 22 of the handle 20 by way of continuous arcuate shanks 24. It is noted that the arcuate shank extends in a plane generally parallel to the axis of the instrument handle with the outermost arc portion extending outwardly of the plane defined by the outer edges of the handle such as shown by the lines A—A in FIG. 2. Further, the cutting blade 23 is connected to the arcuate shank 24 by way of a short straight shank segment 24A which is oriented transversely with respect to the plane of the arcuate shank and preferably at an obtuse angle A-1 with respect thereto. The cutting blade, however, will be oriented at an acute angle A-2 with respect to the plane of the arcuate shank. In this manner, the outer portion of the arcuate shank will urge surrounding cheek tissue or a patient's tongue away from the area being scaled or curettaged during patient treatment. The length of the shank segment 24A will vary to any length, as needed and will be shorter on anterior instruments and longer on posterior instruments and may be between approximately 3 to 6 mm or more. What is important is that the cutting blade be somewhat covered or be within the "umbrella" of the arcuate shank to ensure that adjacent cheek and tongue tissues are maintained in spaced relationship from the cutting blade. FIG. 3A shows the angular relationship of the plane of the arcuate shank and the planes of the shank segment and cutting blade on an instrument having a buccal approach whereas FIG. 3B shows the relationships of an instrument having a lingual approach.

Such an enlarged arcuate configuration for the shank will not only prevent accidental injury to adjacent cheek and mouth tissue but will also enable the practitioner to have a better view of the area being treated. In determining how far the shanks should extend outwardly of the plane A—A of the handles of the instruments of the present invention, it should be noted that the radius of curvature, such as shown at R in FIG. 2, must exceed the radius R-1 associated with a given handle. Preferably, the shank should extend outwardly of the plane A—A by a distance equal to or greater than the radius R-1 of the instrument.

With reference to FIGS. 4 and 4A of the drawings, cross sectional views through two types of conventional cutting blades for curettes (as shown if FIG. 4) or scalers (as shown in FIG. 4A) are disclosed. It should be noted in each embodiment that the cutting edges 25 and 25' which engage the surface of the tooth T are generally oriented at approximately 70 degrees with respect to the surface of the tooth. Further, the upper surfaces 26 and 26' of the cutting edges are shown as being relatively straight between the cutting blades 25 and 25' and the outer edges 27 and 27' of the cutting blades identified at 12 and 12'.

With particular reference to FIGS. 5-8, several embodiments of improved cutting blades of the present invention having altered cross-sectional configurations are disclosed in greater detail. These cutting blades will be described as cutting blades 23A-23D each having a cutting edge 28A-28D which engages the surface of a tooth T at the preferred generally 70 degree angle associated with most conventional scalers or curettes. However, unlike conventional scalers and curettes, the upper surfaces 29A-29D of the four embodiments are shown as including a generally grooved or concave surface portion. In FIG. 5, a portion of the upper surface is shown as including a groove 29A which is generally concave in configuration. In FIG. 6, the upper concave area 29B is somewhat shortened as there is no outer cutting edge as there is reflected with the embodiment of FIG. 5. In FIG. 7, the upper surface includes a V-shaped trough or groove 29C which is formed between the inner cutting edge 28C and an outer cutting edge 30C. In FIG. 8, the V-shaped trough or groove is somewhat offset as shown at 29D due to the structure including only a single cutting edge 28D and a rounded outer edge 30D.

With the embodiments of the invention shown in FIGS. 5-8, as the cutting edges 28A-28D are raised relative to the recessed areas 29A-29D, material which is scraped will be collected in the concave grooves and retained therein as the practitioner urges the instrument vertically relative to a tooth or root of the tooth during normal scaling and curettaging. As scraped material will be trapped within the groove or channel of the cutting blade, such debris may be effectively removed and prevented from falling between the tooth and the gum wherein such material could otherwise cause possible infection and irritation.

With reference to FIG. 9, the length of the grooves 29A-29D of each of the embodiments of the present invention may be varied but should preferably extend for approximately at least 2 millimeters or more along the length of the cutting blade. In this respect, the grooves should terminate inwardly approximately 0.3 mm from the outermost end 31 of each of the cutting blades and also inwardly of the shank segment 24 associated with each of the dental instruments incorporating such cutting blades.

With reference to FIG. 10, a cross section of another embodiment of scaler or curette blade 32 is shown. In this embodiment, the lower surface 33 of the blade is tapered downwardly to form a slightly rounded and blunted wedge 34. The wedge may be used to gently separate gum tissue from the surface of teeth as the blade 32 is introduced therebetween. Such a structure will be of particular advantage for use in those areas where the gum tissue is already irritated.

It should be further noted that each of the embodiments of the present invention may also be used on ultrasonic and vibratory type dental instruments.

I claim:

1. In a dental instrument such as a scaler or a curette which includes a handle having at least one end portion and having a cutting blade which is connected to the end portion by an intermediate shank and wherein the handle has elongated surfaces which extend generally parallel to the elongated axis of the handle, the improvement comprising, said shank being defined by a generally continuous arcuate portion which extends from said end portion of said handle to an outer end, said arcuate portion extending in a first plane, a shank segment extending transversely with respect to said first plane of said arcuate portion and from said outer end thereof, and said cutting blade extending at an angle from said shank segment so as to be generally transverse with respect to said first plane.

2. The dental instrument of claim 1 in which said arcuate portion extends in a plane substantially parallel with the elongated axis of the handle, and said shank segment extends at an obtuse angle with respect to said first plane with said cutting blade extending at an acute angle with respect to said first plane.

3. The dental instrument of claim 2 in which the handle has a first cross sectional radius, said arcuate portion includes an intermediate section, said intermediate section extending outwardly in spaced relationship with respect to the elongated axis of the handle a distance greater than said radius.

4. The dental instrument of claim 3 in which said arcuate portion is defined by a second radius, said second radius being at least twice the dimension of said first radius.

5. The dental instrument of claim 2 in which said shank segment is between approximately 3.0 to 6.0 mm in length.

6. The dental instrument of claim 1 in which the cutting blade includes an outer tip, a cutting edge and an upper surface extending inwardly of said cutting edge, a groove formed in said upper surface of said cutting blade, said groove extending along a portion of the length of said cutting blade and having an outer portion terminating inwardly of and spaced from said tip thereof.

7. The dental instrument of claim 6 in which the cutting blade includes a lower surface, said lower surface being tapered inwardly relative to and away from said upper surface to thereby form a wedge.

* * * * *